United States Patent [19]
Marshall et al.

[11] Patent Number: 5,921,920
[45] Date of Patent: Jul. 13, 1999

[54] INTENSIVE CARE INFORMATION GRAPHICAL DISPLAY

[75] Inventors: Bryan E. Marshall; Carol Marshall, both of Wynnewood; C. William Hanson, Radnor, all of Pa.

[73] Assignee: The Trustees of the University of Pennsylvania, Philadelphia, Pa.

[21] Appl. No.: 08/764,493

[22] Filed: Dec. 12, 1996

[51] Int. Cl.⁶ .................................................. H61B 5/00
[52] U.S. Cl. .................................................. 600/300
[58] Field of Search .................................... 600/300, 301, 600/484, 523–525, 529, 920–925; 128/903, 904

[56] References Cited

U.S. PATENT DOCUMENTS

| | | | |
|---|---|---|---|
| 5,206,807 | 4/1993 | Hatke et al. | 600/525 X |
| 5,262,944 | 11/1993 | Weisner et al. | 128/922 X |
| 5,544,649 | 8/1996 | David et al. | 600/301 |
| 5,623,925 | 4/1997 | Swenson et al. | 600/301 |

OTHER PUBLICATIONS

Berzuini, et al., "Bayesian networks for patient monitoring," *Artificial Intelligence in Medicine*, vol. 4, pp. 243–260, 1992.

Chambrin, et al., "Computer–assisted evaluation of respiratory data in ventilated critically ill patients," *Int J Clin Monit Comp*, vol. 6:211–215, 1989.

Dojat, et al., "A knowledge–based system for assisted ventilation of patients in intensive care units," *Int. Journal of Clinical Monitoring and Computing*, vol. 9:239–250, 1992.

Effken, et al., "Making the Relationships Visible: Testing Alternative Display Design Strategies for Teaching Principles of Hemodynamic Monitoring and Treatment," *American Medical Information Assoc. Inc.*, pp. 949–953, 1994.

Hayes–Roth, et al., "Guardian: A Prototype Intelligent Agent for Intensive–Care Monitoring," *Artif Intell Med*, vol. 4:165–185, 1992.

Miller, "Medical Diagnostic Decision Support Systems—Past, Present, and Future," *J Am Med Informatics Assoc*, vol. 1:8–27, No. 1, Jan/Feb. 1994.

Mora, et al., "Intelligent Patient Monitoring and Management Systems: A Review," IEEE Engineering in Medicine and Biology, pp. 23–33, 1993.

Rixen, et al., "'Sepsis/SIRS,' Physiologic Classification, Severity Stratification, Relation to Cytokine Elaboration and Outcome Prediction in Posttrauma Critical Illness," *The Journal of Trauma: Injury, Infection and Critical Care*, vol. 41, No. 4, pp. 581–598, 1996.

Rutledge, "Dynamic Selection of Models for a Ventilator–Management Advisor," *Amer Med Inf Assoc*, vol. 34:344–350, 1994.

Rutledge, et al., "The design and implementation of a ventilator–management advisor," *Artificial Intelligence in Medicine* vol. 5:67–82, 1993.

Seiver, "A decision class analysis of critical care life–support decision–making," *Int. Journal of Clinical Monitoring and Computing*, vol. 10:31–66, 1993.

(List continued on next page.)

*Primary Examiner*—Samuel Gilbert
*Attorney, Agent, or Firm*—Woodcock Washburn Kurtz Mackiewicz & Norris LLP

[57] ABSTRACT

This invention describes a patient monitoring system which creates graphical displays of various pulmonary and other patient functions so that physicians and clinicians can quickly and accurately make decisions about the patient's care based on the graphical displays while in the intensive care unit. Patient functions are monitored and pulmonary models are implemented to graphically reveal relationships between the basic information input to the system from monitoring devices and the models so that physicians can utilize the revealed relationships to make informed accurate diagnoses and design therapeutic plans concerning the patient.

10 Claims, 5 Drawing Sheets

OTHER PUBLICATIONS

Sun, et al., "Simulation of Hemodynamics and regulatory mechanisms in the cardiovascular system based on a non-linear and time–varying model," *Simulation*, vol. 59, No. 1, pp. 28–36, Jul. 1992.

Uckun, et al., "Model–based diagnosis in intensive care monitoring: The YAQ approach," *Artificial Intelligence in Medicine*, vol. 5:31–48, 1993.

Uckum, et al., "Qualitative modeling as a paradigm for diagnosis and prediction in critical care environments," *Art Intell Med*, vol. 4:127–144, 1992.

INTENSIVE CARE INFORMATION GRAPHICAL DISPLAY

FIELD OF THE INVENTION

This invention relates generally to methods and apparatus for displaying graphical information. More specifically, this invention relates to interactive information processing systems and methods therefor wherein derived values from information are displayable in relation to the information so that observers of the information and the derived values can easily understand relationships between the information and the derived values which were heretofore unrevealed.

BACKGROUND OF THE INVENTION

Information intensive environments require observers of the information to make quick decisions in short time frames. An example of an information intensive environment is found in medicine in the surgical intensive care unit ("SICU"). In fact, a SICU is among the most information intensive environments in modern medicine. Monitors display vital functions of increasing sophistication but the displays are not uniform in design nor are they integrated, so that it is necessary for the clinician to survey several storage devices (including written records) at one time. Decisions in the SICU are often critical and urgent, and there is increasing pressure to reduce the time an individual is under intensive care and an increasing number of patients requiring such care. These conflicting considerations, that is, increased information and reduced time to assimilate it, create critical junctures in patient care in the SICU which may impair or delay the physician or other care giver from making accurate and safe judgments about the patient's immediate care. Current information visualization techniques are simply inadequate to facilitate the need for quick decisions.

Respiratory monitoring is a more specific example of the need in the SICU for fast and accurate decision making based on a great deal of critical information assaulting the physician in a short time. A few concepts are fundamental to respiratory care. Some, such as the three compartment model for gas exchange and the pressure/volume relationships for lung ventilation are approximately quantified in every patient as a conceptual basis for representing pathophysiology. Others such as the pulmonary vascular pressure/flow relationships or the effects of the distribution of ventilation/perfusion ratios are understood in theory but seldom quantitatively because they are technically difficult to measure or are approximate. Traditional and selected pulmonary measurements together with the volume-pressure model ("V/Q-P/Q Model") provide a means to estimate all these relationships and, for the first time, permit the interactions between the gas exchange and the blood flow properties of the lung in an individual patient to be assessed.

A large part of physician training is geared towards teaching physicians how to evaluate the changing variables presented by patients. This is achieved most often by development of mental representations of prototypical diseases and modified by experience, since it is well known that human beings can only accurately retain about seven items in short term memory. Such dependence on mental processing is inefficient and potentially inaccurate. There have been few attempts to display this complex data graphically and in such a form as to assist the clinician in the SICU or in other information intensive and demanding environments to process the data to derive quick decision-making abilities effectively.

Prior applications of computer-based information processing systems in medicine have been directed at pulmonary disease and particularly at respiratory intensive care. The earliest systems were directed at evaluating pulmonary function tests or providing smart alarms of malfunctions. Variations of these systems and improved data collection, display and calculation of some physiological variables have led to monitoring devices of the type that are now to be found in all intensive care units. Subsequent work has explored the use of computer based physician assistants, for example, to wean patients from mechanical ventilation, but the input required from the user was excessive.

Automatic data entry led to improved display of individual values and trends, but the applications were too narrow and research interest rapidly moved away from providing assistance to providing advice to physicians on diagnosis. However, even for the most sophisticated systems, the pathophysiology of cardiopulmonary function that they encompass is less advanced than that of an intensivist, and none of these systems has been adopted clinically. "Expert" systems have also been developed to inject artificial intelligence aspects into medical computer environments, but have generally been ineffective, since they cannot accurately make decisions in the place of physicians or clinicians.

Prior cognitive monitoring devices and methods therefore do not provide the physician or clinician with efficient and effective means for quickly analyzing data in an information-rich environment. There thus exists a long-felt but unfulfilled need in the monitoring art for methods and systems that will allow physicians or other clinicians to draw conclusions and make decisions as they are being bombarded by myriad forms of information in stressful environments such as the SICU.

SUMMARY OF THE INVENTION

The above mentioned long-felt needs are met and problems solved by interactive information processing systems provided in accordance with the present invention. The systems preferably comprise a database adapted to receive and store information provided to the database at specified intervals, the information being indicative of basic observations, a computer for calculating derived values based on the information, the derived values being capable of conveying the information to an observer so as to reveal relationships to information as emergent features, and a monitor to display the information and the derived values in the revealed relationships.

Methods of graphically displaying information in an information intensive environment also satisfy the above mentioned long-felt needs. Preferably, the methods comprise the steps of gathering the information on a database from sources of the information in the environment, calculating derived values from the information, and displaying the derived values and the information as a function of revealed relationships between the information and the derived values.

Even more preferably, the present invention includes intensive care unit monitoring systems. The systems comprise a plurality of monitoring devices which produce data indicative of information about a patient in the unit, a processing sub-system which calculates values derived from the information on the basis of models of patient functions so as to reveal relationships between the information and the values, and a display subsystem which graphically displays the revealed relationships as a function of the information and the derived values so that physicians treating the patient can quickly make decisions about the patient's care based on the revealed relationships.

The present invention allows use of Ehrhart's cognitive system design framework to implement an interactive, bedside, computer-based information processing system sometimes referred to herein as "the V/Q-P/Q Assistant" for the SICU. The V/Q-P/Q Assistant will enable expert and resident physicians and nurses to arrive at therapeutic decisions more efficiently by providing easier access to accumulated data, improved analysis of the pathophysiology and the ability to simulate the responses of a specific patient to therapeutic trials (virtual therapy). The systems and methods of the present invention may implement an existing model, like the V/Q-P/Q Model, combining conventional clinical methods with both ventilation/perfusion ratio distributions and pulmonary vascular pressure/flow relations, and are also readily adaptable to new respiratory and pulmonary models which may be developed in the future. Furthermore methods and systems described and claimed herein are adaptable for use in other medical regimes, and in other environments which require fast processing of information to make quick decisions.

The invention will be best understood by those with skill in the art by reading the following Detailed Description of Preferred Embodiments in conjunction with the drawings which are first described briefly below.

DETAILED DESCRIPTION OF PREFERRED EMBODIMENTS

Figure 1:
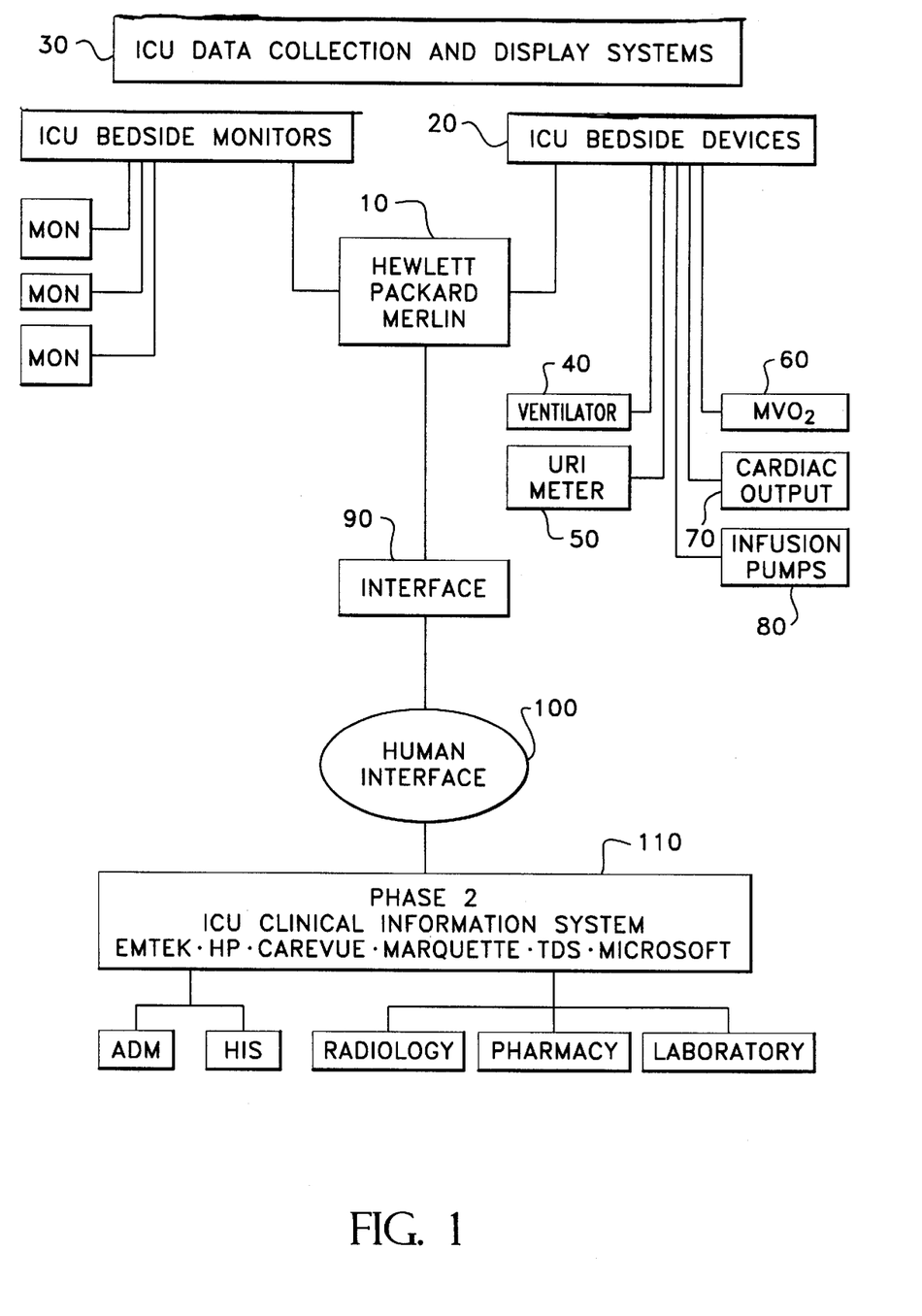
FIG. 1 is a block diagram of an intensive care unit collection and display system in accordance with the present invention.

Referring now to the drawings where like reference numerals refer to like elements, FIG. 1 is a preferred embodiment of an intensive care unit ("ICU") monitoring system which can be implemented in a SICU or other environment where a massive amount of information must be assimilated by an observer who must then make critical decisions in a short amount of time. By way of example, the present invention is described with respect to a preferred system which functions in a SICU or ICU; however, it will be recognized by those with skill in the art that the present invention is generally applicable to any interactive information processing system which processes information in an environment where an observer must make quick and efficient decisions.

To that end the present invention will utilize a computer processor for calculating derived values from the information such that the derived values are capable of conveying the information to an observer so as to reveal relationships to the information. In this manner, emergent features of the information may be gleaned by the observer in ways which were not heretofore apparent, thereby allowing the observer to make decisions based on the revealed relationships and emergent features. This will facilitate efficient and effective decision making in environments where massive amounts of information must be assimilated and acted upon in real or near-real time. The present invention thus utilizes concepts in cognitive science which combines theories of knowledge with usage of computers to attain a complete system to assist the physicians in making decisions in the SICU. This approach involves defining pathophysiological states from a multi-component data stream which is then used to create a therapeutic management plan for the patient. This will assist the physicians and clinicians in the SICU to evaluate the data and other information more rapidly and to explore the pathophysiological basis in greater depth so that therapeutic decisions can be reached more accurately.

Preferably, the system comprises several standard devices which have been used in the past to monitor patients in the SICU such as a data gathering device 10 which is adapted to receive and store information at specified intervals in time. The information will be indicative of basic observations being performed in the SICU from patients made by devices 20 and monitors 30. The devices will be, for example, ventilators 40, meters 50, MVO2 devices 60, cardiac outputs 70, infusion pumps 80 and any other devices which provide information in the SICU which must be acted upon with urgency. Similarly, the monitors 30 provide myriad forms of information which are also stored on the data gathering device. In a more preferred embodiment, the data gathering device is the MERLIN bedside monitor and database available from the Hewlett-Packard Company of Palo Alto, Calif., which provides a data stream known to those with skill in the art. The MERLIN monitor has been used in SICUs in the past to gather, store and route information. Data from the monitors and bedside devices is conventionally bussed to the MERLIN monitor through standard RS232 cables.

An interface 90 which is preferably connected to the MERLIN monitor 10 is adapted to process the information received and routed by the MERLIN 10. The interface 90 preferably comprises an object-oriented database and is implemented in the C++ computer language (or other object-oriented program environment). The object-oriented database allows for semantically correct data representation such that patient data is stored as an inheritance hierarchy of defaults, or measured and derived values according to the detail of information received by the MERLIN monitor 10.

The number of individual variables received by the MERLIN monitor 10 and the need to store trends for individual patients, as well as the possibility that many different patients may be monitored at one time in accordance with the invention, means that database management is important in the present invention. As a first step, the measured values generated by the SICU devices 20 and monitors 30 and the values required for and generated by the pathophysiological subroutines by the interface 90 are entered into a data dictionary found in the human interface 100 of the present invention. Each of the required values are characterized by Attribute, Description, Format, Range, Default, Units, Aliases, Uniqueness, Not-Null, Multi-Valued, Hierarchical Level, Relevance, Reliability, Table Name, Source, Indexed, Comparable Index and Comments. The data dictionary provides a reference source and record for both finding data and keeping track of variables.

The variables include, but are not limited to, Patient ID, date, barometric pressure, height, weight, sex, age, body temperature, heart rate, cardiac output, mean systemic arterial and pulmonary arterial pressure, pulmonary artery occlusion pressure, central venous pressure, inspired oxygen concentration, end tidal and mixed expired carbon dioxide concentrations, positive end-expiratory pressure, peek inspiratory pressure, respiratory rate, tidal volume and arterial and mixed venous blood oxygen, carbon dioxide, pH, base excess and hemoglobin, hemoglobin P50 and hematocrit. From these values together with a number of constants as will be described in more detail below, the software of the human interface 100 derives values for body surface area, cardiac index, stroke volume, systemic vascular resistance, pulmonary vascular resistance and conductance, arterial and mixed venous blood oxygen and carbon dioxide contents, arteriovenous blood gas content differences, oxygen consumption, oxygen delivery, alveolar oxygen and carbon dioxide tensions and alveolar to arterial tension differences, pulmonary venous admixture or shunt percentage, minute volume, physiologic alveolar and anatomic dead space, and pulmonary compliance.

The software then predicts normal values for cardiac output, minute volume, dead space, oxygen consumption, oxygen delivery, systemic and pulmonary vascular resistance, arterial oxygen tension/fractional inspired oxygen concentration (PaO2/FIO2) and base excess. When the multiple inert gas tensions are measured, estimates will be replaced by measured values for mean ventilation/perfusion ratio, natural logarithm standard deviation of the distribution of ventilation/perfusion ratio distribution for up to 50 compartments, the compartmental blood flow, ventilation and gas exchange and all the estimates of gas exchange inefficiency and including other gases (i.e., nitric oxide or inhalational anesthetics V/Q-P/Q Model adds estimates of the normal pressure/flow relationships with fluid bed volume and the independent pulmonary vascular characteristics (i.e., number, constriction, hypoxic pulmonary vasoconstriction responsiveness, compliance of large and small arteries, large and small veins and the capillary bed. The computations and output requirements are then preferably organized hierarchically by the interface software. All the data is based on age, sex, weight and height.

As can be seen from the above, a vast amount of data is received at the human interface 100 and processed to arrive at a myriad of derived values. It is extremely difficult for a physician or clinician to retain and interpret this data without some form of graphical aid, and a cognitive system that maximizes efficient mental processing of the information. In accordance with the invention, software associated with the human interface 100 "chunks" into several bins or usage groups the information which is composed of raw data routed through the MERLIN 10 and the calculated derived values. The information can be chunked into any appropriate number of bins for the particular application. In the present embodiment, the information is chunked into five usage groups. These are preferably the LUNG usage group wherein pulmonary ventilation, perfusion and gas exchange are quantified; the HEART usage group wherein pressure, flow and right and left heart pump functions are quantified; the KIDNEY usage group wherein fluid and balance are monitored; the METABOLIC usage group wherein acid-base and nutrition are monitored; and the NEUROLOGIC usage group wherein the central and peripheral nervous systems are monitored. These chunked usage groups form the basis for displaying the information to a physician or clinician in the SICU with varying degrees of graphical sophistication to be discussed below in greater detail.

After the interface 90 processes the data from the devices, it is preferable to input the information to the human interface 100 which will allow the physician or clinician to review the information and to derive values therefrom in such ways so as to allow the physician or clinician to make fast and efficient decisions about the patient by recognizing relationships between the data and derived values.

Most preferably, the human interface 100 will provide access to five levels of increasing display sophistication and integration. At the first level, the outputs of the continuous clinical monitors will be sampled at ten minute intervals and stored in a relational database together with results from blood gas and other intermittent measurements. These data will be available for inspection as values in an organized spreadsheet format. On a second level, from the basic observations a number of derived values are calculated (i.e., dead space, pulmonary shunt, oxygen delivery, etc.) from traditional equations. These values will be combined with those of the first level in configural displays designed to reveal relationships as emergent features and characteristic patterns.

On a third level of increasing display sophistication, the V/Q-P/Q Model is preferably implemented to estimate the volume of atelectatic lung, equivalent pulmonary vascular bed patency and standard deviation of the distribution of the V/Q Ratio. This third display level allows the system to calculate interrelationships among the derived values so that the physician can make educated guesses about the necessary therapy and how changes in the patient's variables will be effected by changes in therapy.

At the fourth level, the human interface 100 implements additional functional techniques that are used to measure more precisely the values estimated at level three to characterize the pulmonary vascular responsiveness to hypoxia and other vasoactive agents. This fourth yet more sophisticated graphical display eliminates the need for guessing and produces accurate measurements of complex interdependent patient variables.

Finally, at a fifth level of sophisticated graphical display, pulmonary gas exchange and blood flow of patients is characterized by the V/Q-P/Q Model and thereafter responses of that patient to changes in any of the existing parameters will allow simulation of therapeutic alternatives. This level of display sophistication is termed "virtual therapy" wherein the responses of the computer representation of the patient can be tested by "trials" of therapy to assist the physicians in their development of a therapeutic plan that can instituted in the patient.

It should be recognized that the information to be input to the human interface 100 can flow from several medical departments or areas. Thus, hospital admissions (ADM), histology (HIS), radiology, pharmacy, laboratories and other medical departments in a hospital or medical organization can input information to the human interface 100 from, for example, a clinical information system 110 which, similar to the MERLIN 10 described above, provides a data stream with other relevant patient information which can be factored into the various levels of display sophistication.

Most errors or inefficiencies in prior monitoring systems have resulted from inadequate attention to the pre-implementation phases of the system. In a preferred embodiment, Ehrhart's cognitive systems engineering design framework, which is well known to those with skill in the art, is implemented in accordance with the invention to obtain monitoring systems for use in the SICU. Ehrhart's system is described in COGNITIVE SYSTEMS ENGI- NEERING: HUMAN-COMPUTER INTERACTION DESIGN FOR DECISION SUPPORT, Center of Excellence in Command Control, Communications & Intelligence, George Mason University, Fairfax, Va. (August 1994), the teachings of which are incorporated herein by reference. In this approach the design of the V/Q-P/Q Assistant of the present invention is broken down into four stages, namely, the nature of the sources of information in the SICU, analysis of the physician's tasks that the computer is to assist, the form of the human-computer interaction and the options for implementation.

In accordance with Ehrhart's approach, the effectiveness of decision making in complex highly-dynamic environments like the SICU depends on correctly matching information processing capabilities with cognitively demanding tasks. Recognition of a familiar pattern by a physician or clinician invokes a rule-based response while novel situations required deeper knowledge and formal reasoning. An experienced clinician creates a mental representation of a patient, recognizes similarities to patients previously treated and makes inferential leaps based on mentally simulating courses of action. However, errors occur when the response level does not match the situation because essential data is overlooked or is integrated inappropriately. These errors are particularly likely in the SICU because the data stream is so intense and unrelenting.

The human-computer decision-making performance is enhanced when the task allocation and information sharing involved with the user-computer cooperation is matched to both the environmental characteristics and the response requirements. Use of the computer may be ineffective or human performance may even be degraded when these properties are mismatched. The primary objective of human-computer interaction is to ensure that the user gets the right information at the right time with the right level of detail.

To describe the graphical levels with further detail, in the first level the display of information and/or derived values by the human interface is accomplished in a spreadsheet format. In this simple format, all of the information is stored as data in a database, and the screen display is simply in a spreadsheet. The original measured values from the monitors or intermittent samples, and the values derived routinely, are grouped approximately by function (i.e., ventilation, gas exchange, acid-base balance, pulmonary circulation and cardiac function). Historic trends and further details are obtained in additional screen spreadsheets by scrolling or touching 'hot' buttons. This format is designed to follow the present clinical practice in the SICU of collecting all relevant data on expanded paper spreadsheets which are completed manually by various members of the support staff. At first this display may be prototyped as a fixed display with data entered manually. When the data collection, sampling and storage distribution procedures are completed the spreadsheet will be active at the bedside and the relative reliability of these two forms of record keeping can be compared. Subsequently the database may be an object-oriented one but this will be transparent to the user, except perhaps for the increased response speed.

At the second, more sophisticated level of data display, the information of level 1 is displayed graphically. This embodiment is termed throughout as "screen displays." The level two screen displays comprise the configural displays illustrated in FIG. 2, for example. These graphical displays contain all the data of the spreadsheets but in a form that provides more integration of the data and promotes intuitive understanding of connections between the data (referred to as "emergent features"). Time trends and further details will also be available by touching 'hot' buttons on the screens. In addition, it is preferable to include displays such as those of FIGS. 3A and 3B which show, for example, the time trend for oxygen delivery and arterial oxygen content, respectively.

Referring again to FIG. 2, for applications of the present invention in the SICU to monitor pulmonary functions, the system preferably displays standard measurements and plots these measurements on the periphery of the screen. Thus, information such as base excess pH (BASE EXC), PaO2/FlO2, Systemic Vascular Condition (SYST VASC), Pulmonary Vascular Condition (PULM VASC), Oxygen Constriction (OXY CONS), Oxygen Delivery (OXY DELV), Change in Pressure (THOR COMP), and minimum volume (MIN VOL) can be displayed in traditional format.

Figure 2:
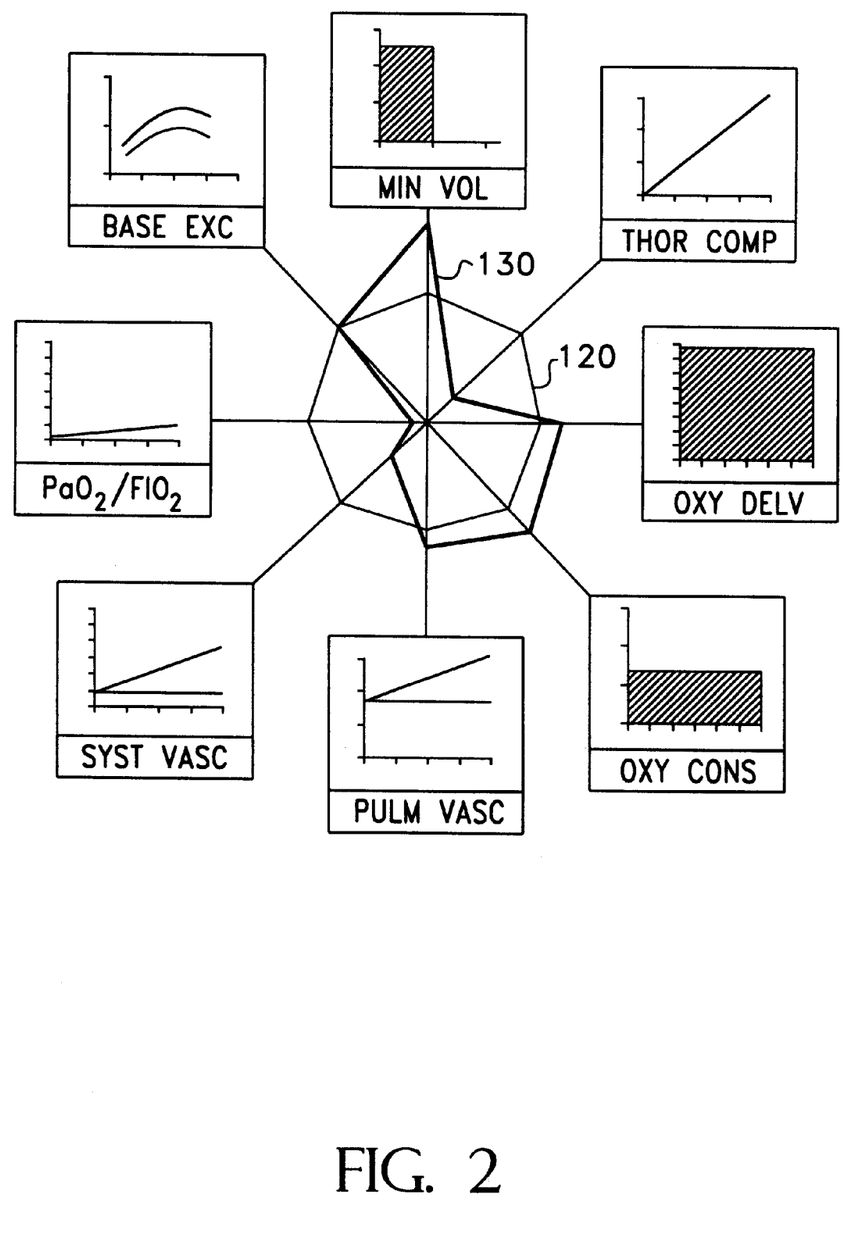
FIG. 2 is a graphical depiction of a set of pulmonary system values that are generated in a SICU and how this information provides a set of derived values which expose new relationships for the information so that the physician or clinician can understand these relationships to make quick and accurate decisions.
Figure 3A:
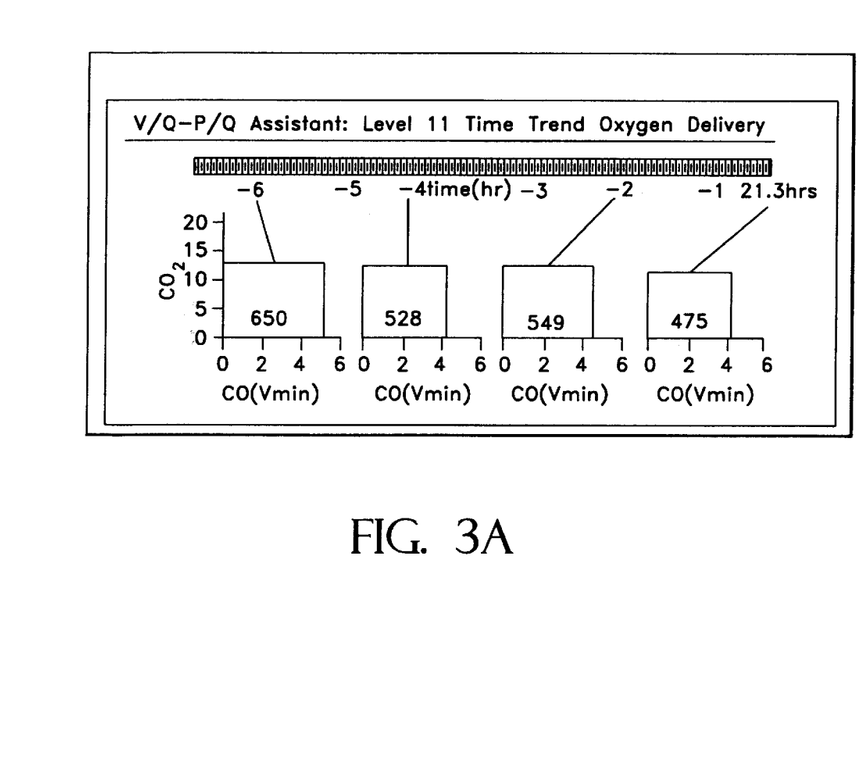
FIGS. 3A and 3B are graphical displays in accordance with the present invention which show the time trend for oxygen delivery for a patient in the SICU, and the arterial oxygen content for the patient, respectively.

The eight displays around the periphery have been selected for their emergent features or properties. The arrangement is intended to provide a rational sequence such that ventilatory concerns are summarized at the top, oxygen delivery and metabolism on the right, pulmonary vascular properties at the bottom and inefficiency of oxygen exchange on the left. For each display the time trends can be accessed by touching hot buttons which can optionally be placed at the origin, and further detail about values that are composed of additional variables can be obtained by touching the hot buttons optionally placed on the relevant axis.

The present state of the eight principal variables, namely minute ventilation, thoracic compliance, oxygen delivery, oxygen consumption, systemic and pulmonary vascular resistance, PaO2/FlO2 and base excess are expressed with relation to predicted normal values as a radial plot 120, the spokes of which point to the source of the data. This radial FIG. 120 generates a pattern 130 around the normal values where values greater than normal expand the figure and reduced ones contract it. The form of this pattern is intended to provide assistance with recalling the magnitude and direction of the changes with particular disease states and with changes in time.

At the third level of display sophistication and integration, the V/Q-P/Q Model calculations can be used to estimate the functional effects of abnormal distributions of the V/Q ratio, lung collapse, loss of vascular bed, altered HPV responsiveness and vasoconstriction from other agonists and at other vascular sites. These calculations use the conventional data of levels one and two described immediately above, but in addition require the physician to entertain an 'educated guess' of the magnitude of the change. The output will consist of special screens to illustrate the nature and influence of the pathophysiologic abnormality.

The purpose of this kind of display sophistication is to allow physicians to explore concepts and suggestions that are often advanced but have hitherto not been possible to pursue at the bedside. Patients admitted to the SICU often present a mixed functional pathology and level three type displays will permit estimating answers to "what if" questions by physicians presented with such complicated pathologies. In this way various individual or mixed impairments can be explored to assist understanding and support a particular management plan.

In a further preferred embodiment, at a fourth level of display sophistication special technique integration displays are provided. The important distinction between this level and the previous level is that here the values for V/Q ratio distribution, atelectatic lung volume, loss and state of vascular bed, HPV responsiveness and vasoconstriction from other sources are the result of special measurements. The results obtained from each of these measurements therefore provides a more accurate representation of the pathophysiologic condition of the patient. If all of these measurements are available, pulmonary hemodynamics, gas exchange and the interrelationships between the two are characterized to a previously unprecedented level. Each measurement will be reached on the human interface 100 by selecting level four and the particular measurement. A new screen will then prompt for the data corresponding to the particular test and the outputs will be displayed on new configural displays. Because the graphical display derived in level four is less familiar than the conventional information discussed previously it is envisioned that there will be opportunities to present the results and concepts in more original ways than have been heretofore displayed.

In the fifth, highly sophisticated display level provided in accordance with the present invention, all of the previous levels may be integrated into a single display. This allows the physician or clinician to engage in "virtual therapy" and to make decisions and diagnoses in quick time and with high confidence. The ability to test a patient's response to a wide variety of virtual therapy is believed to be a particular attribute of the V/Q-P/Q Assistant.

A second ordinate with a slide (not shown in FIG. 2 but shown, for example, at 135 in FIG. 3b) may be optionally placed adjacent to several of the eight peripheral displays. The slide is activated by touch and permits the user to simulate therapeutic trials and observe the changes in the displays, all of which are linked through the V/Q-P/Q Assistant model.

Figure 3B:
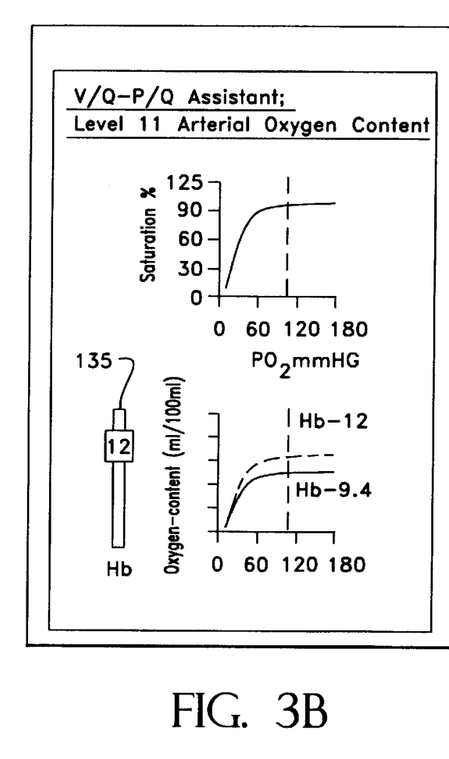

The program recalculates all the values and interdependent effects that results from change in the position of the scroll bar.

For example, increasing the hemoglobin content (FIG. 3A) not only increases the oxygen content and oxygen delivery but also alters the mixed venous oxygen content and tension, the blood pH and carbon dioxide, the stimulus for HPV, the distribution of the V/Q ratios, pulmonary gas exchange efficiency and pulmonary artery pressure and blood flow distribution. These effects are recalculated within 15 seconds and the results shown in a different color or line type on the same displays as the current data. The effects of the change can therefore be compared to the original data and a clearer understanding of these often very complex relationships is obtained. In the final form linked changes will be possible, thus a virtual increase of inspired oxygen tension can be combined with virtual inhalation of nitric oxide and so forth. It is worth noting that the knowledge as to the reliability of the virtual treatment predictions resides in the level of data acquisition and the particular treatment under consideration.

Figure 4:
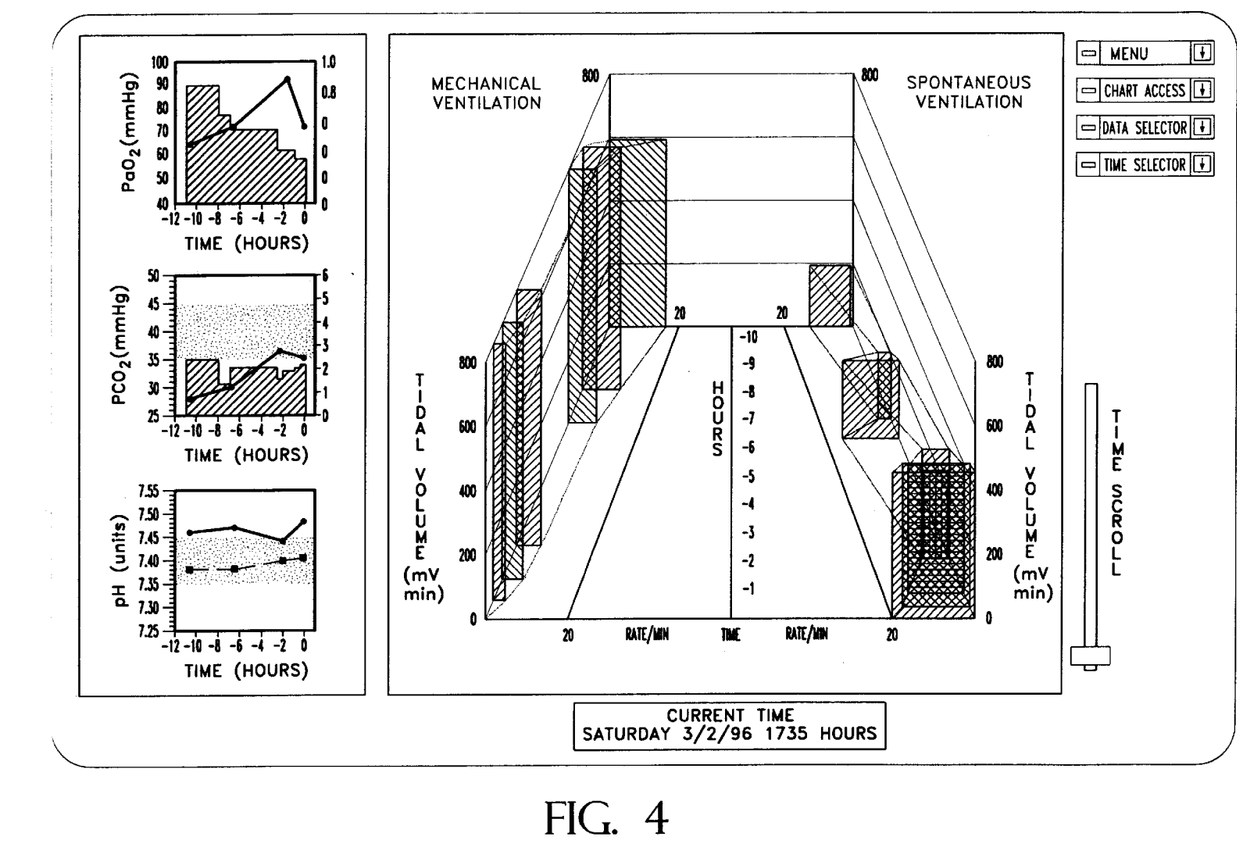
FIG. 4 is graphical depiction of a respiratory monitoring scheme of the present invention wherein derived values have been generated and displayed based on information received from the SICU.

FIG. 4 is an example of a display to aid in weaning patients from mechanical ventilation. As can be seen, the information and derived values shown in the display of FIG. 4 provide clearly the information required for this decision and, by selecting among the myriad variables encountered in the SICU improves the speed and accuracy of the process. The system of the present invention provides software which produces screen displays such as those shown in FIG. 4 which are intended to provide the information to allow the caregiver to rapidly provide their cognitive representation of the patient by careful selection and novel graphical methods of visualizations of this information.

Computer displays that mimic physical devices such as thermometers, gauges and dials are readily associated with similar mental models. More complex information may require the use of already familiar or pictorial forms, appropriate emphasis, emergent features or combinations of these representations. In the practice of cognitive engineering design for human-computer interfaces implemented in accordance with the present invention, the system encompasses an iterative process of planning, design, prototype, evaluation and redesign which has resulted in sophisticated software packages to perform the displays and computations produced throughout. While prototypes of the system use simple paper representations or computer displays for the initial development so that modifications can be rapidly incorporated, new generation systems may use combinations of prior data gathering techniques coupled with newer or more sophisticated techniques to produce system displays that are optimized for the SICU or other information gathering environments.

It can thus be said that the present invention employs cognitive systems engineering to represent information in a form that is appropriate for the mental models employed by the user. The present embodiment of the invention provides a medical cognitive graphics system to meet the dual goals of displaying both low level data and high level concepts, the purpose of which is to aid quick reasoning in a stressful environment.

Figure 5:
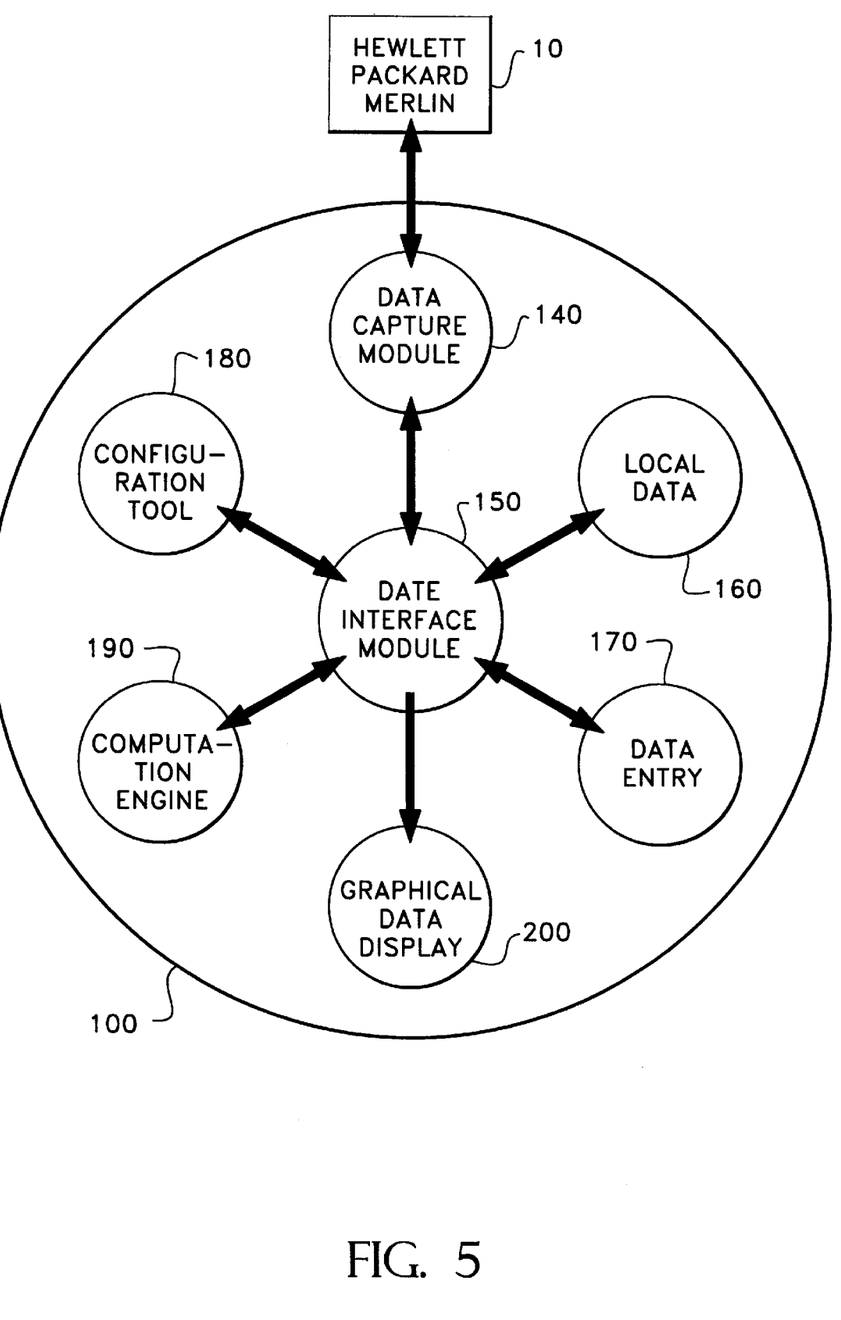
FIG. 5 is a diagram of a preferred flow of information in an intensive care unit of the present invention.

Referring to FIG. 5, a preferred embodiment of the data flow in the human interface 100 system of the present invention is shown. FIG. 5 particularly illustrates the versatility of systems described and claimed herein with respect to data flow and production of the various derived values and graphical displays which are advantageously created thereby. Preferably, the MERLIN monitor 10 inputs information to a data capture module 140 that is implemented in software. As can be seen, data can flow back and forth between a computer which implements the data capture module 140 and the MERLIN monitor 10.

More preferably, a data interface module 150 bidirectionally interfaces with the data capture module 140 and acts to direct data to the remaining software modules and also back to the data capture module 140 according to the particular software protocols which are adapted in accordance with the invention to generate the values for the various display options discussed above. Still more preferably, local data 160 is bidirectionally interfaced to the data interface module 150 and provides data to be used in the computations of derived values. Additionally, manual data may be entered to the system at 170 to provide a complete set of information for the graphical displays.

In still a further preferred embodiment, a configuration tool 180 which is implemented in software communicates bidirectionally with the data interface module 150 and acts to correctly configure the data for accurate representation on the displays of the present invention. A computation engine 190 provides the various mathematical functions necessary so that the values for all of the displays can be calculated. Many computation engines can be used for this function and are commonly available on the market today for this purpose. The data interface module 150 integrates the data received from and acted upon by the various modules of FIG. 5 and outputs this information to a graphical data display module 200 which is then observed by the physician or other clinician at the various kinds of display sophistication which have been described above.

The systems of the present invention implement pulmonary monitoring techniques for the unique graphical displays described herein. In particular, the values required, the monitoring devices that are the sources of these values and the methods already introduced for automatically sampling and storing samples at regular intervals are utilized by the present systems to provide new displays which enhance decision making capabilities in the SICU.

To validate that the data are collected and stored reliably values will be noted manually at specified times and subsequently compared to the stored values. Calibration signals from the monitors are used to create a standard signal set at intervals to provide warning of equipment malfunctions. All continuous data will be sampled and stored at 10 minute intervals, but when the data are 24 hours old the number of data points stored will be reduced to values averaged over 1 hour. Whether further reductions will be appropriate as the data age will be dependent on observing how older data is used. Many different kinds of values can be used to derive the displays. For example, values from intermittent sampling, such as from blood analyses for gas tensions, pH and base excess, will be entered manually, as will the initial data for patient identification and age, sex, height, weight and diagnosis.

The V/Q-P/Q Assistant systems of the present invention can be implemented at the bedside in the SICU. The human interface, data sampling, computations and storage will all be performed by a computer as is generally illustrated in FIGS. 1 and 5. The patient characteristics and identification may be entered manually as may be data from intermittent blood samples and special tests, for example. The outputs of the various monitors and devices that provide information to the system can be accessed by direct RS232 communications port connections between the computer and the monitors and devices. The software of the present invention permits automatic updating and data bussing from each monitoring device to the computer.

As will be recognized by those with skill in the art, the specific arrangement of monitors and devices will vary with particular SICU and data needs of the personnel in the SICU. However, conventional monitors (i.e., respiratory rate, volume, airway pressures and metabolic monitors) can be used for any such system configuration. For example, the Puritan-Bennet® 7200 ventilator and metabolic attachment, pressure transducers and cardiac outputs devices from Nelcor®, as well as instrumentation that is conventionally available from the Abbott Company, Hewlett-Packard and Baxter can be employed. Various proprietary instruments may also be interfaced to the system if particular data needs are required which are not readily available from the market place.

For completeness, it is worth mentioning that in a specific embodiment of monitoring systems of the present invention, characterization and utilization of several pulmonary monitoring techniques will be used. For example, and not intending to limit the invention in any way, the "inert gas technique" will be used to produce data for the system. In the inert gas technique, if all alveoli received the same proportionate amount of blood flow and ventilation (V/Q ratio), the lung would be ideally efficient. In practice, they do not and the greater the spread of the distribution of V/Q ratios around the mean the less efficient the gas exchange. These ideas were recognized in the three compartment model of 1946, which remains the principal model used by physicians for representing gas exchange. This model was recognized to be only a gross approximation because it lumps all abnormalities affecting carbon dioxide as dead space and all those affecting oxygen as venous admixture (shunt), defining the rest of the lung as exchanging gas ideally.

But not until 1974 was a practical method published for deriving the distribution of ventilation/perfusion ratios (V/Q) as a fifty compartment model. Gases are executed or retained in a lung compartment as a simple function of gas solubility and the V/Q ratio. The principle of the method is to infuse six inert gases with increasing solubilities. From the gas tensions measured in mixed venous and arterial blood samples, and mixed expired gas samples the overall excretion and retention curves are calculated as functions of the solubility. These relationships allow derivation of the pair of ventilation and perfusion ratio distribution curves that best account for the data.

The distributions are expressed in terms of their means and standard deviations of the natural logarithm of the V/Q (ln SD(V/Q)), from which all respiratory gas exchange values can be calculated and compared. Although the insights provided by the MIGET technique, well known to those with skill in the art, are profound, it is technically so demanding that use remains confined to only a dozen or so laboratories. The concentrations of the gases are very small, and the technical problems are mainly due to analysis by gas chromatography which requires not only that the gases be extracted from the blood into a gas phase but also that the individual blood gas solubilities be derived so that gas tensions can be calculated. These manipulations are very time consuming and the source of most of the errors.

Attempts to analyze by mass spectrometry in the past have failed due to persistent stirring and memory effects. Because of advances in materials and mass spectrometry in the development of a Membrane Inlet Mass Spectrometer (MIMS) by collaborations of the inventors of the subject matter herein claimed and disclosed which has recently occurred, these problems have not only been overcome, but it is possible to permit very rapid (5 minutes) analysis of the multiple inert gas tensions directly in small (5 ml) blood samples. The MIMS analysis therefore permits the MIGET estimation of ventilation perfusion ratio distributions to become a real time, repeatable, bedside method. This is a specialized tool that can be integrated into the systems of the present invention.

The V/Q-P/Q model is also utilized in the present invention. This model starts from a generalized pressure/flow curve (P/Q model) that is based on biodynamic measurements of the number, size, compliance and effective flow viscosity for a complete lung vascular bed. Subsequently the V/Q and P/Q models have been combined into the V/Q-P/Q Model. The existing conditions are the basis for a single pressure/flow curve with no HPV. The blood flow is predicted, also in the absence of HPV, for up to 49 compartments (the 50th is anatomic dead space with no blood flow) where one is shunt flow, and the distribution of the remaining 48 is described by the mean V/Q and the standard deviation (ln SD(V/Q)). For the conditions existing in a particular patient, the alveolar gas and end capillary blood gas composition is calculated for each compartment. From the mixed venous oxygen tension and the alveolar oxygen tension the stimulus for HPV is derived so that the single pressure flow curve is converted to the family of pressure/flow curves with HPV, representing each compartment. The one pulmonary artery pressure at which the sum of combined compartment flows equals the normal cardiac output is found iteratively. Because the mean V/Q and the ln SD(V/Q) are altered the calculations are repeated until the derived arterial oxygen tension does not differ by more than 0.1% and the final distribution of V/Q ratios is derived.

The calculation can proceed in either direction and includes the effect of alveolar instability when high oxygen concentrations are breathed. Furthermore, the influence of loss of vascular bed (by embolism, thrombosis, lobectomy, etc.), vascular narrowing whether passive (fibrosis, hypertrophy) or active (HPV or other causes of constriction at any vascular site, or any other pharmacologic or pathophysiologic change in specific vessel properties are incorporated. This technique is described in the allowed U.S. patent application Ser. No. 08/238,294, filed Jul. 26, 1994, the teachings of which are specifically incorporated herein by reference.

The analysis from the V/Q-P/Q Model is most compatible with a lung in which 45% of the alveoli is atelectatic, 20% of the vascular bed has been obliterated (by thromboembolism), the remaining bed is constricted by endogenous or exogenous agonists, and hypoxic pulmonary vasoconstriction is greatly diminished. With these characteristics the model simulates closely the observed response to inhaled nitric oxide and would presumably be able to help guide the selection of other therapeutic choices also. It is this power to present pathophysiologic understanding in greater functional detail and to simulate therapeutic maneuvers at the level of clinical complexity that makes the implementation of the V/Q-P/Q Assistant of the present invention so powerful.

The present V/Q-P/Q Model is written in Turbo Pascal and C. In order to facilitate later programming and model refinements in the current program the model will be analyzed as a flow diagram logical model listing all the mathematical equations. A structured pseudo-code version written in English will make explicit the rationale and assumptions. Strict modularity according to structure and hierarchy will be adhered to and the computer aided software design tools included in Easy Case System Designer (by Evergreen Case Tools, Inc.) will be used.

It is envisioned that several specific enhancements of the program will further enhance the systems of the present invention. These include biochemical properties of fibrotic vascular segments, longitudinal vascular distribution of pharmacological properties, incorporation of airway properties and factors determining lung water balance.

Additionally, the advantage of inducing pulmonary vasodilation by infusing prostacyclin to characterize the very rapid metabolism of the drug so that its actions are confined to the pulmonary circulation has been desired in the prior monitoring systems. However, it is expensive and less familiar for use in intensive care. In contrast, nitroprusside and nitroglycerine, while inducing generalized vasodilation, are used routinely in clinical practice. For the study the routine measurements of gas exchange and pulmonary hemodynamics will be performed while ventilating with 100% oxygen in the absence and presence of the infused vasodilator irrespective of which drug is used. With the V/Q-P/Q Model, these measurements provides basis for predicting the equivalent volume of atelectatic lung, the vascular bed availability and the extent of HPV and other sources of vasoconstriction.

Similarly, pulmonary vasodilation by inhalation of nitric oxide provides vasodilation only in ventilated regions of the lung. For the particular purposes of this application an inhaled dose of 40 ppm of NO is sufficient in all patients. In the presence of 90% oxygen, comparison of the change in arterial oxygen tension with the change of pulmonary vascular resistance provides evidence of the responsiveness of the pulmonary circulation to HPV and of the extent to which other vasoconstrictor influences (both endogenous and exogenous) are active. Pulmonary vasoconstriction during the infusion of any general vascular constrictor (i.e., norepinephrine, neosynephrine etc.) not only increases pulmonary vascular resistance but depending on the extent of HPV, also increases arterial oxygen tension. These observations provide evidence of general vascular reactivity and HPV. Because support of the circulation by vasoactive drugs is commonplace in these patients the measurement is readily available. The combination of an infused vasoconstrictor with inhaled NO provides further insight because the effectiveness of NO depends on having an active but reversible vasoconstriction and a significant pulmonary shunt and/or V/Q Ratio maldistribution. If the additional vasoconstriction does not enhance oxygenation during inhalation of NO and if vascular resistance is little effected by NO and the infused vasoconstrictor, then the factors causing increase of vascular resistance are morphologic (i.e., loss or narrowing of vascular bed by thrombosis, embolism or fibrosis).

Finally, it is worth noting that the V/Q-P/Q Ratio distribution will be calculated from the traditional multiple inert gas excretion method but using the new method developed based on the MIMS analysis of the gas concentrations directly in blood samples. The advantages of this approach are that the speed and ease of analysis makes the estimation of V/Q Ratio distributions practical for real-time, bedside use.

It should be understood that the above mentioned data gathering techniques and methods which have been utilized to implement the systems of the present invention are but examples of the kind of techniques that can be used to provide meaningful data to a physician. Those with ordinary skill in the art will readily appreciate that any type of data analysis technique for pulmonary care can be used with the present systems to obtain useful graphical displays which have also not heretofore been attainable. The present invention is intended to cover all such future uses.

The systems and methods of the present invention are robust and can be used repeatedly to obtain clinically useful graphical displays. The capabilities of the V/Q-P/Q Assistant of this invention are versatile, and will provide information not currently available. The content and connectivity of the screens and displays produced hereby are natural to an observer and easy to evaluate. Such results have not heretofore been achieved in the art.

There have thus been described certain preferred embodiments of graphical display systems and methods provided in accordance with the present invention. While particular embodiments have been described, it will be appreciated by those with skill in the art that modifications are within the true spirit and scope of the present invention. The appended claims are intended to cover all such modifications.

What is claimed is:

1. A method of graphically displaying patient information to a clinician on a display, comprising the steps of:
   gathering clinical patient data from patient monitoring equipment;
   inputting static patient data representing characteristics of the patient;
   storing said clinical patient data and said static patient in a database;
   processing said clinical patient data and said static patient data to determine values of derived patient parameters indicative of the patient's physical condition;
   displaying said derived patient parameters;
   accepting simulated changes to said clinical patient data from a clinician;
   determining anticipated changes to said derived patient parameters caused by said simulated changes to said clinical patient data; and displaying the anticipated changes to said derived patient parameters, whereby the relationships among the derived patient parameters may be determined by changes in displayed values of said derived patient parameters.

2. A method as in claim 1, comprising the further step of displaying the derived patient parameters with predicted normal values of said patient parameters derived from said clinical patient data and said static patient data in said database.

3. A method as in claim 1, comprising the further steps of grouping the derived patient parameters by body function, storing the derived patient parameters in said database as historical trend data, and displaying the grouped derived patient parameters with corresponding historical trend data stored in said database.

4. A method as in claim 3, comprising the further step of displaying said grouped derived patient parameters with predicted normal values for said derived patient parameters determined from said historical trend data.

5. A method as in claim 4, wherein said grouped derived patient parameters and said predicted normal values for said derived patient parameters are displayed in respective radial plots which indicate the changes in the derived patient parameters and the relationships of these values with respect to predicted normal values over time and over changes in the patient's condition.

6. A monitoring system which graphically displays patient information to a clinician, comprising:

a patient database;

at least one patient monitor which gathers clinical patient data from the patient and stores said clinical patient data in said database;

an input device which inputs static patient data representing characteristics of the patient into said database;

a processor which processes said clinical patient data and said static patient data to determine values of derived patient parameters indicative of the patient's physical condition;

a graphical display which displays said derived patient parameters; and an input interface which accepts simulated changes to said clinical patient data from a clinician, wherein said processor determines anticipated changes to said derived patient parameters caused by said simulated changes to said clinical patient data and provides the changed derived patient parameters to said display whereby the relationships among the derived patient parameters may be determined by the indicated changes in said derived patient parameters.

7. The monitoring system of claim 6, wherein said processor calculates predicted normal values of said patient parameters derived from said clinical patient data and said static patient data in said database and provides the predicted normal values to said display.

8. The monitoring system of claim 6, wherein said processor groups the derived patient parameters by body function and stores the derived patient parameters in said database as historical trend data, and said display displays the grouped derived patient parameters with corresponding historical trend data stored in said database.

9. The monitoring system of claim 8, wherein said processor determines predicted normal values of said patient parameters derived from said clinical patient data and said static patient data in said database and provides the predicted normal values to said display for display with said grouped derived patient parameters.

10. The monitoring system of claim 9, wherein said grouped derived patient parameters and said predicted normal values for said derived patient parameters are displayed by said display in respective radial plots which indicate the changes in the derived patient parameters and the relationships of these values with respect to predicted normal values over time and over changes in the patient's condition.

\* \* \* \* \*